United States Patent

Goodman

[11] 4,119,093
[45] Oct. 10, 1978

[54] INTEGRAL PATIENT-LIMB SURGICAL DRAPE SYSTEM

[76] Inventor: Floyd G. Goodman, East Lansing Medical Plaza, 4528 S. Hagadorn Rd., East Lansing, Mich. 48823

[21] Appl. No.: 726,449

[22] Filed: Sep. 24, 1976

[51] Int. Cl.² .............................................. A61B 19/06
[52] U.S. Cl. ................................................ 128/132 D
[58] Field of Search ............... 128/132 R, 132 D, 292, 128/157

[56] References Cited

U.S. PATENT DOCUMENTS

| 1,724,443 | 8/1929 | Wheeler | 128/292 X |
| 2,591,783 | 4/1952 | Craddock | 128/132 D |
| 3,030,957 | 4/1962 | Melges | 128/132 D |
| 3,536,006 | 10/1970 | Ludwig | 128/132 R |

OTHER PUBLICATIONS

Ruby Products Co. Inc. 2-1-60, (Gyn Sheet).

Primary Examiner—Lawrence W. Trapp
Attorney, Agent, or Firm—Philip J. Rosewarne

[57] ABSTRACT

A surgical drape including a sheet with a fenestration through which extends a somewhat conical or contoured covering for receiving and isolating, from the rest of the patient, that portion of a patient's limb or extremity upon which surgery is to be performed. The covering is collapsed about the fenestration telescopically or accordian-like and is surrounded by four folded, overlapping stacks of the sheet. Layers of reinforcing material and liquid-impermeable material are provided contiguous to the fenestration.

21 Claims, 25 Drawing Figures

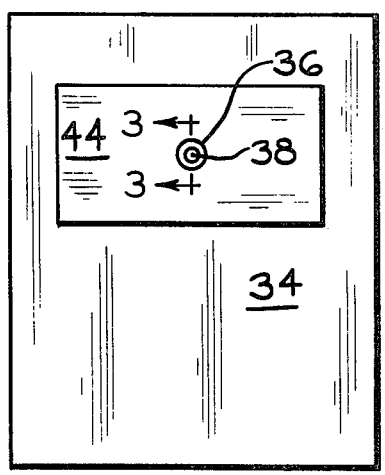
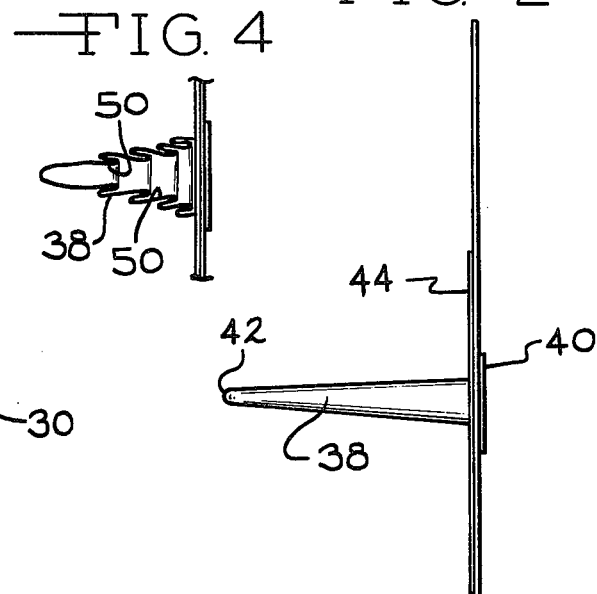
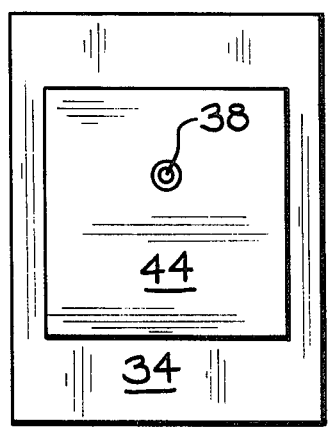
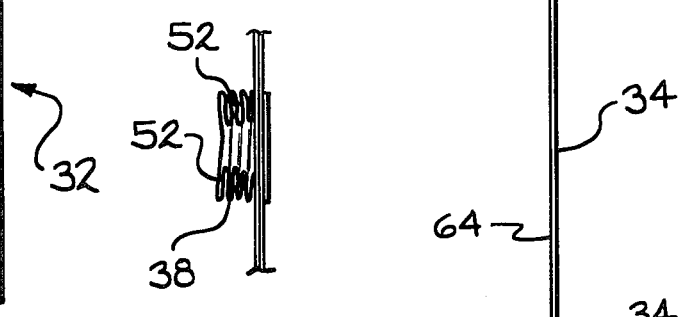
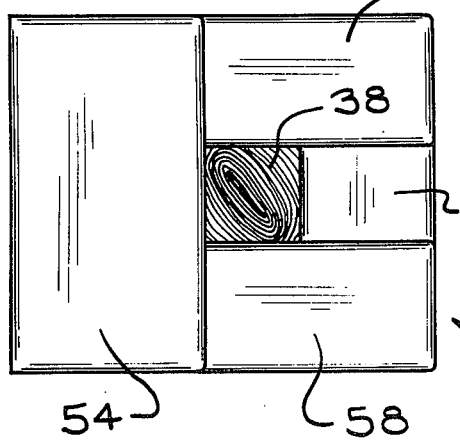
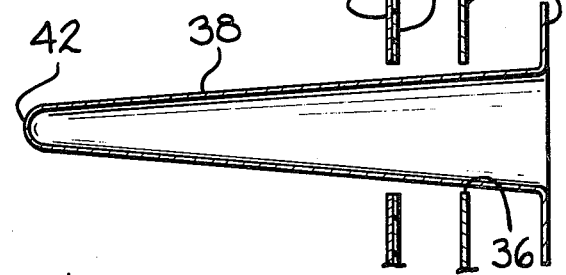

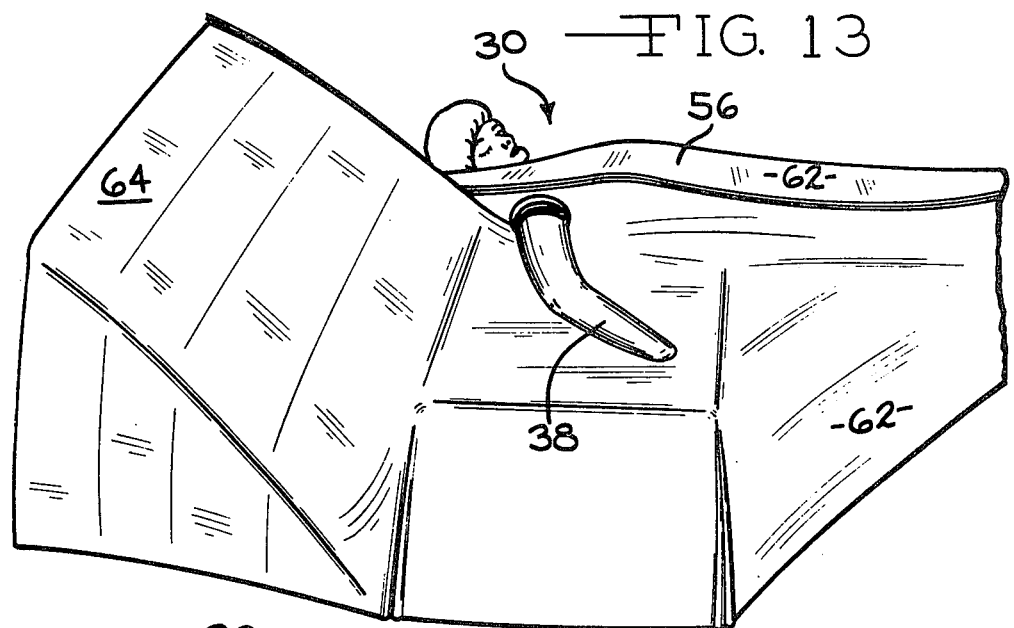
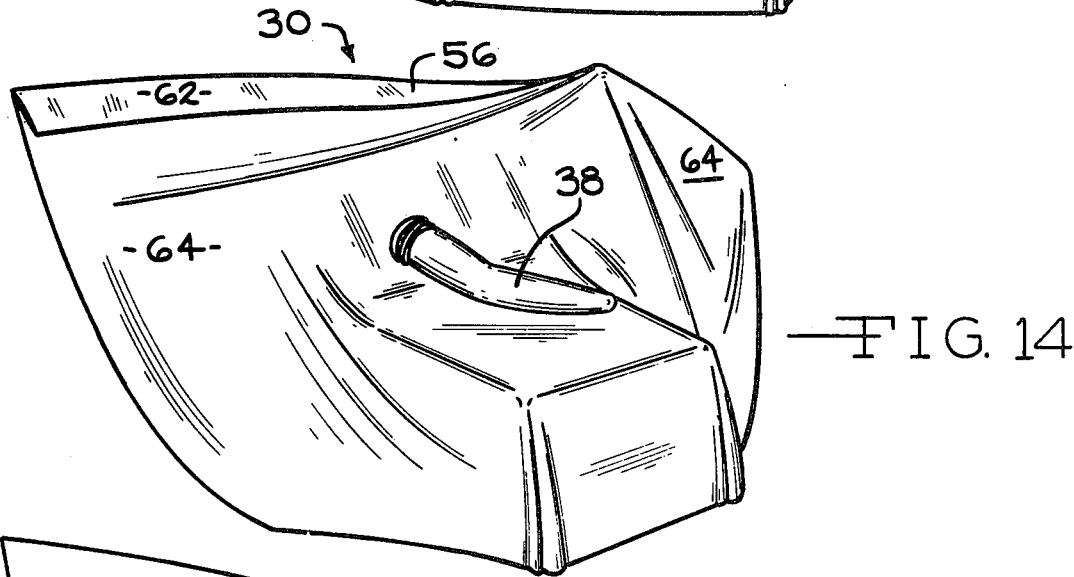
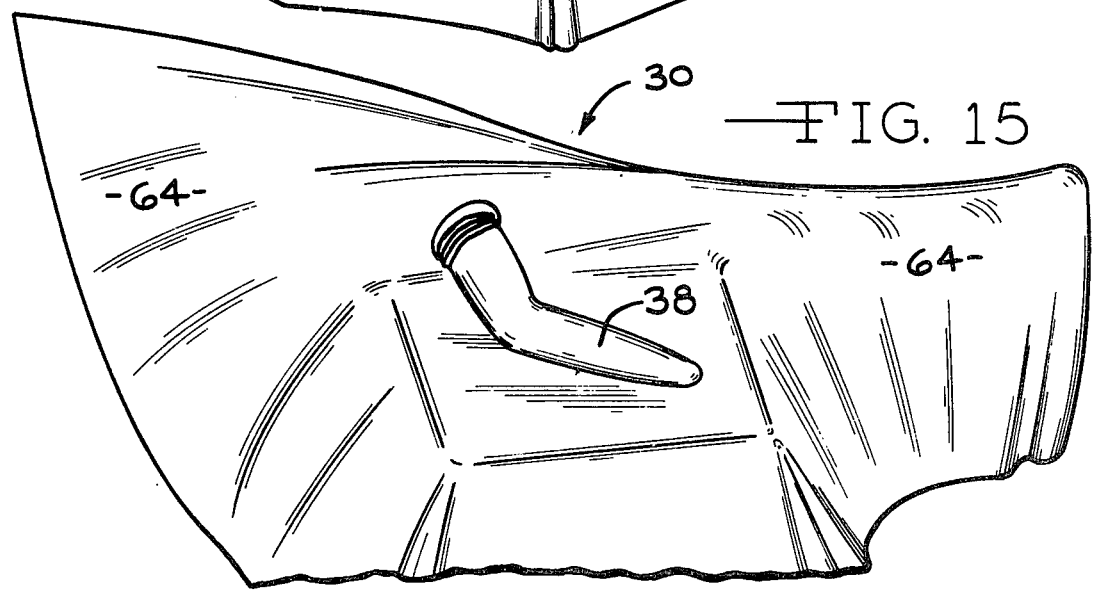

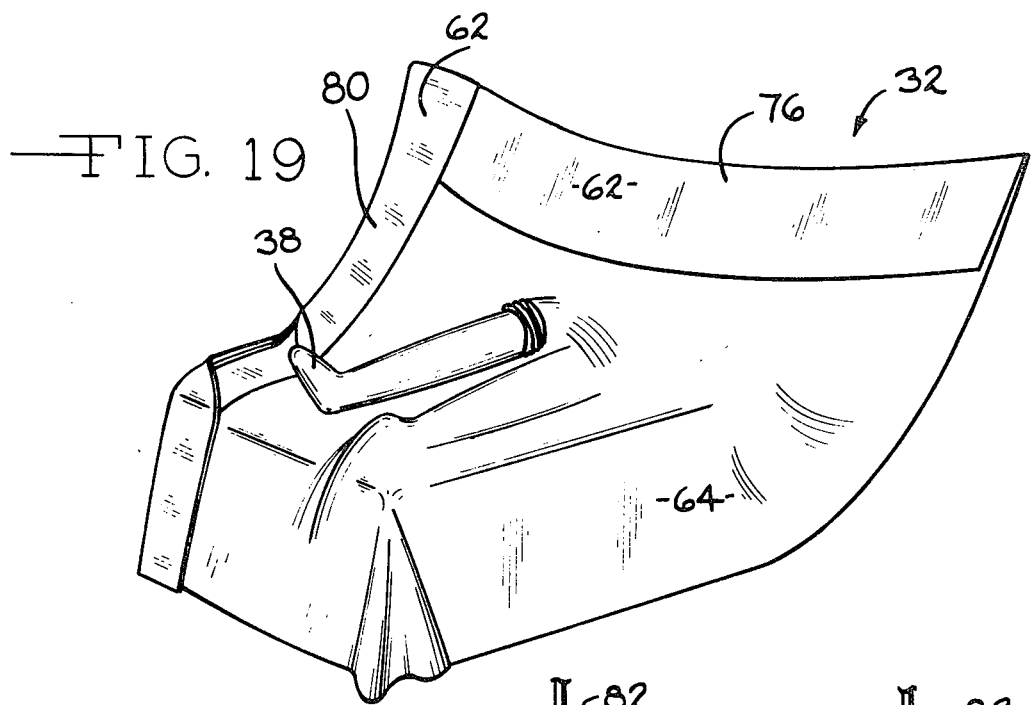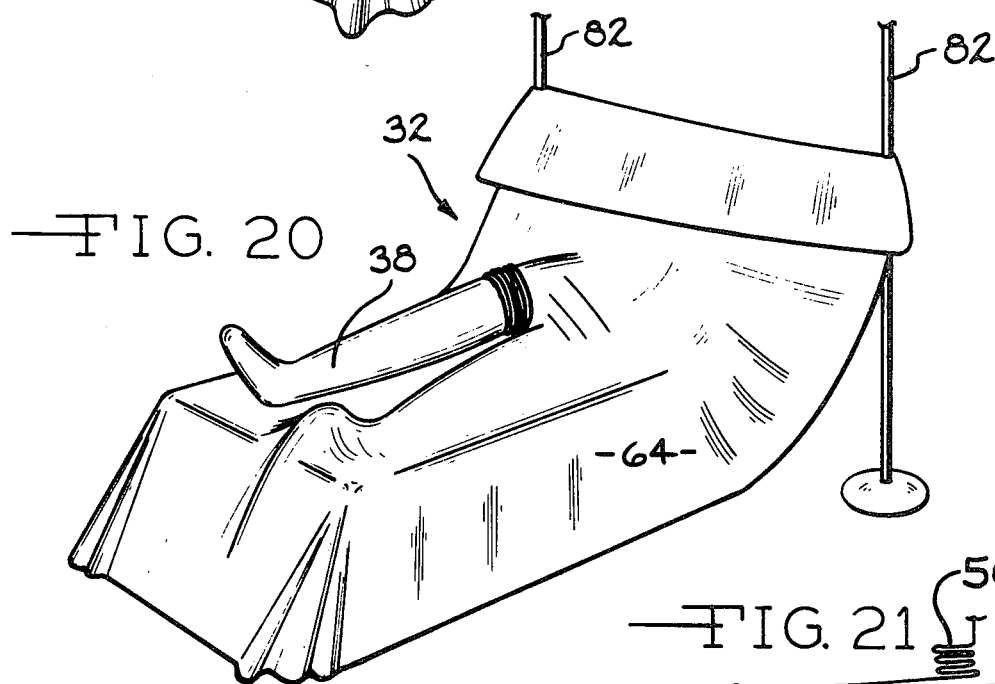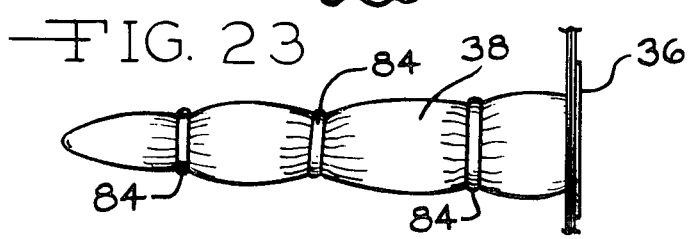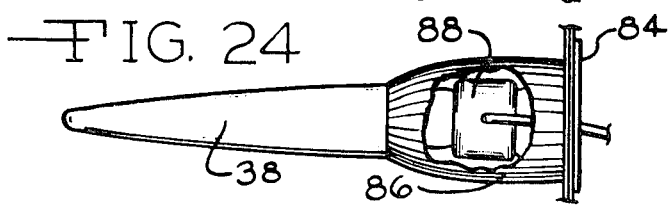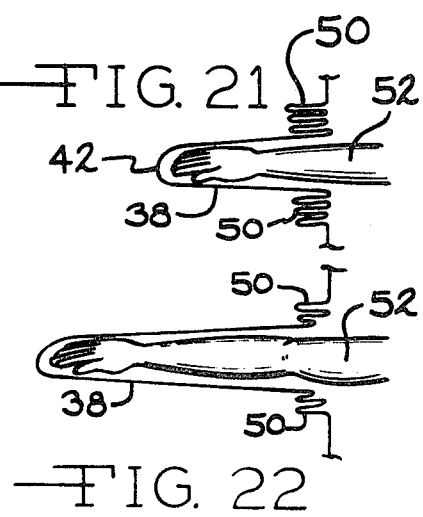

INTEGRAL PATIENT-LIMB SURGICAL DRAPE SYSTEM

BACKGROUND OF THE INVENTION

1. Field of the Invention

The present invention relates generally to surgical drapes and more particularly to a surgical drape for a limb upon which surgery is to be performed.

2. Description of the Prior Art

In the past, it has been a standard procedure to drape extremities utilizing a number of individual, singularly folded, linen sheets to provide a sterile field to cover the entire patient, yet leave the extremity accessible and free to be manipulated into the desired position. This has been formerly accomplished by allowing one nurse (unsterile) to elevate the limb while the surgeon and one or more assistants, all of whom are sterile, position the drapes under and over the extremity, the torso, etc. During this procedure, the sterile surgical team comes in close contact with the (unsterile) nurse out of necessity, and therefore is risk, knowingly or unknowingly, of contamination. A sterile, rolled, knit stocking may be placed over the distal end of the extremity and unrolled to cover the limb and provide a sterile cover for the surgeon to safely manipulate. During the unrolling of the stocking, a sterile hand not uncommonly may come in contact with an unsterile area, again thereby, either knowingly or unknowingly, contaminating the operative field.

The covered limb is then laid on the sterile bottom drapes and more sheets, usually five to seven in number, are introduced to cover the area above the extremity. The bottom sheets are then attached to the top sheets by means of sterile "towel clips." At this point, another possible source of contamination is introduced in that the points of the "towel clips" pass through the sterile outer edges of the drapes and may come into contact with the contaminated underside. It is not unusual during the course of a surgical procedure for a "towel clip" to pop open and fall onto the sterile field, again contributing to general contamination.

The above factors outlining frequent causes of contamination, combined with the time-consuming procedure of placing multiple sheets and sometimes followed by rolling the stocking over the limb and clipping the sheet edges together, impose a constant threat to the patient, with loss of aseptic conditions and increased anesthesia hazard by prolongation, thereby rendering currents standards of contemporary draping systems entirely inefficient and undesirable.

The reusable linen draping system poses additional undesirable factors which are subjected to the problems of quality control including imperfect laundering, hand folding, steam sterilization (which may introduce unknown contamination due to the drape packs being stored while still damp), undetected holes and tears, storage problems due to bulky packaging and possible contamination during transportation between laundry and surgical sites.

The prior art has generally been directed to covering extremities (such as legs) so as to isolate a surgical area other than the limb, from the limb itself. A typical surgical legging drape is illustrated in U.S. Pat. No. 3,777,749 wherein the leg is to be draped as an unprepared area to prevent contamination of the surgical site by the unprepared leg. For obstetrical or gynocological operative procedures, prior art devices have included a drape having separate leggings, as illustrated in U.S. Pat. No. 3,039,957, or separate leg drapes as in U.S. Pat. No. 3,693,618. In all of these patents, the object or area of surgery is other than the extremity which is draped. Similarly, these prior art systems are rather complicated, involving a multitude of elements interrelated such that their application to the patient is cumbersome, time-consuming and susceptible to undesirable contamination.

The most simple surgical drape available on the market provides a single sheet of drapable material having an enlarged aperture covered with a second material which is cut by the surgeon to provide a fenestration through which is passed the limb to be operated on. This drape is used with a second drape for the limb to provide a completely draped system. It should be noted that this system, though involving a reduced number of drapes, still involves the judgment and skill of the surgeon or assistant nurse to cut the fenestration in the second material so as to minimize the exposure of the patent's body under the drape area. Even with an accurately cut fenestration, a perfect fit with the limb cannot be achieved.

Thus, there exists a need for a draping system which isolates the surgical area of an extremity from the rest of the patient's body, which at the same time is convenient to use and not susceptible to high degrees of contamination.

SUMMARY OF THE INVENTION

The problems of the prior art are overcome by providing a compact, pre-folded, disposable integral limb-torso surgical drape for utilization during surgery on a limb. The drape includes a single sheet having a fenestration therein through which extends an elongate, somewhat conical covering for the limb upon which the surgery is to be performed. The limb covering is packaged collapsed about the fenestration in a telescopic manner such that portions of increasing diameter are sequentially exposed as the limb is advanced through the fenestration. Alternately, the limb covering may be collapsed accordian-like with the increasing diameter portions laying one on top of the other so as to also sequentially expose the sections. The sheet is folded in four stacks surrounding the collapsed limb covering so as to completely cover the surgical surface of the sheet. A reinforcing layer is provided on the patient's side of the drape contiguous to the fenestration and covers the point at which the contoured limb covering is mounted to the sheet. A layer of liquid-impermeable material may be provided on the exterior side of the sheet, also contiguous to the fenestration.

The four stacks of folded sheet are arranged in an overlapping manner so that the topmost stack is unfolded to provide the surface upon which the limb will rest during surgery. The remaining stacks may be folded and overlapping so that the bottom stack is opposite the first stack and the two remaining stacks are between the top and bottom stacks and unfold along the length of the patient. Alternately, the top stack may include a second opposite top stack covering two stacks, 90° from the top stack, wherein the top stacks unfold along the length of the body and the bottom stacks unfold 90° relative to the length of the body of the patient. The sheet of material is of sufficient length and width to completely cover the patient and to isolate the patient from the surgical team and the area of surgery. Also, a strap or a plurality of straps may be provided to encompass the limb covering for dividing the covering so as to isolate the area of surgery from the fenestration, and to prevent the covering from slipping about on the limb.

OBJECTS OF THE INVENTION

An object of the present invention is to provide an integral, compact, prefolded disposable surgical drape for utilization during extremity surgery.

Another object of the present invention is to provide a drape being assembled and prefolded in such a manner as to eliminate the undesirable contamination and clumsiness of those devices of the prior art.

A further object of the invention is to provide a drape of unitary construction which is applied to the limb to be operated on and the patient in a flowing single-phase pattern of application, rather than in a broken series of multi-step procedures which prolong the operative process and increase the chances of contamination.

Still another object of the present invention is to provide a surgical drape which totally isolates the surgical area of a limb from the remainder of the patient's body.

A still further object of the invention is to provide a prefolded compact integral surgical drape wherein areas of increased diameter of a contoured limb covering portion are sequentially exposed, thereby reducing the probability of contamination of the interior of the covering during the insertion of the limb.

Other objects, advantages and novel features of the present invention will become apparent from the following detailed description of the invention when considered in conjunction with the accompanying drawings.

BRIEF DESCRIPTION OF THE DRAWINGS

FIG. 1 is a planar view of a preferred embodiment of the surgical drape of the present invention for use with the upper extremities or limbs;

FIG. 2 is a side view of the surgical drape of FIG. 1;

FIG. 3 is a partial exploded side view of the limb covering and sheet taken along lines 3—3 of FIG. 1;

FIGS. 4 and 4A are partial side views of the limb covering of FIG. 1 collapsed telescopically and accordian-like, respectively;

FIG. 5 is a plan view of the surgical drape of FIG. 1 with the limb covering telescopically collapsed and the sheet folded;

FIG. 6 is a plan view of another preferred embodiment of the surgical drape of the present invention for use with lower extremities or limbs;

FIGS. 7–15 are perspective views of the sequence of application of the surgical drape of FIG. 1, as applied to a human arm;

FIGS. 16–20 are perspective views of the sequence of application of the surgical drape of FIG. 6, as applied to a human leg;

FIGS. 21 and 22 are cut-away side views of an arm extending the limb covering of FIG. 4;

FIG. 23 is a side elevation of FIG. 1, including straps; and

FIG. 24 is a side elevation of a modification of the surgical drape of FIG. 1 to accommodate a tourniquet.

DESCRIPTION OF THE PREFERRED EMBODIMENTS

Figure 16:
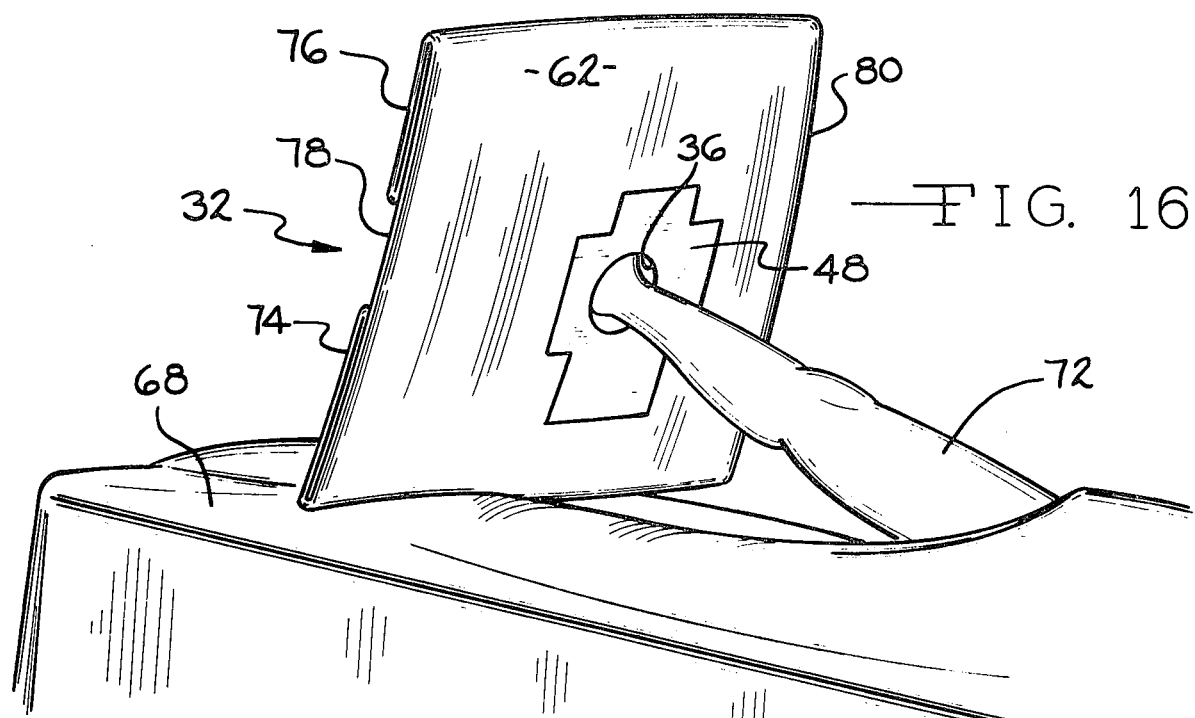
Figure 17:
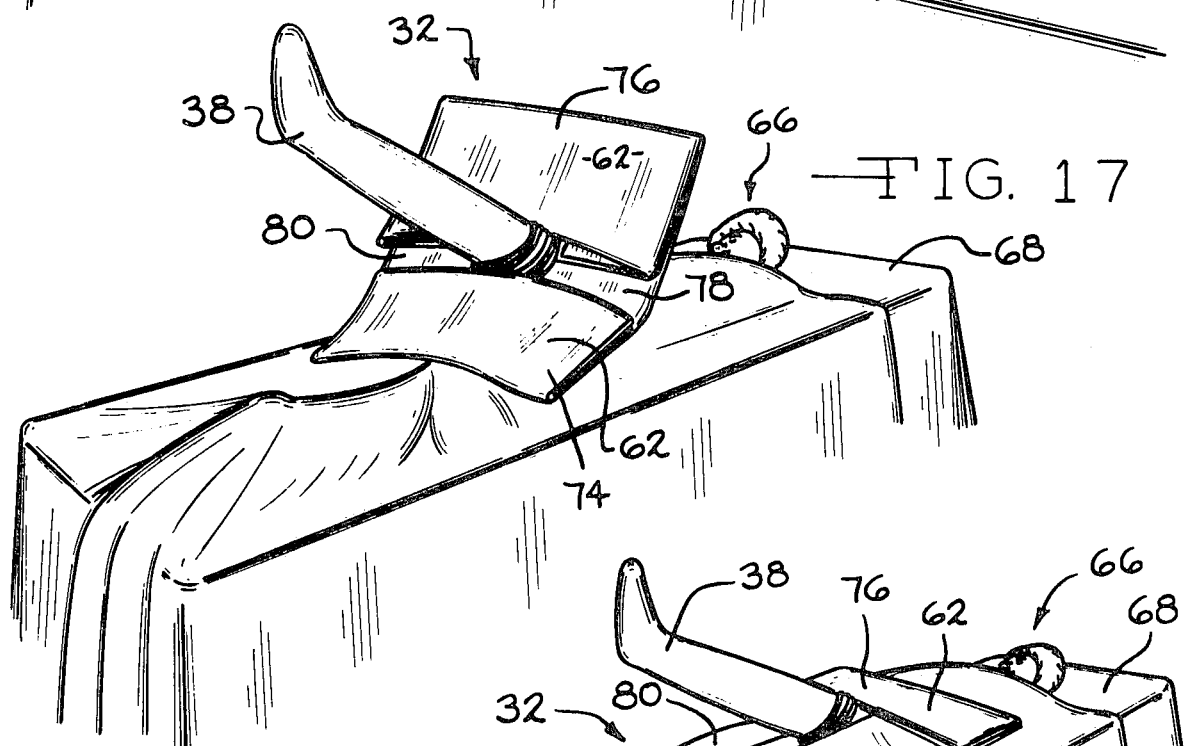

FIGS. 1–5 illustrate a preferred embodiment of a surgical drape 30 for upper extremities or limbs and FIG. 6 illustrates a preferred embodiment of surgical drape 32 for lower extremities or limbs. These surgical drapes 30 and 32 include a rectangular sheet of flexible material 34 having a single fenestration 36 therein. The sheet 34 may be made of any material, but a non-woven flexible material (which may be a paper product) is preferred since it reduces the cost of the total drape so as to make it disposable. Extending through the fenestration 36 is a generally conical covering, sleeve, or limb sock 38 which is the covering for the extremity upon which surgery is to be performed. The covering 38 has a base 40 attached to the patient's side of sheet 36 and is closed at a truncated end 42. A layer of reinforcing material 44 and a layer of liquid-impermeable material 46 are secured to the exterior surface of sheet 34 contiguous to the fenestration 36 as illustrated in FIG. 3. A second reinforcing layer 48 may be provided on the patient's side of sheet 34 as illustrated in FIG. 16. Reinforcement 48 not only reinforces the sheet 36, but also covers the attachment of base 40 to sheet 34. It should be noted that reinforcement layer 48 may be used in combination with reinforcement layer 44 or in lieu thereof.

The specific dimensions of sheet 34 may vary, depending upon the size of the patient, since an essential feature of the present invention is that sheet 34 be large enough to completely cover the patient and isolate the patient from the surgical team and the area of surgery. Similarly, the specific size and shape of reinforcing layer 44 may vary depending upon its specific use. Though the specific location of fenestration 36 varies depending on whether it is to be used with the upper or lower extremities (as illustrated in FIGS. 1 and 6), it has been found convenient that fenestration 36 lie along the center longitudinal axis of sheet 34. Sheet 34 is preferably made of any disposable non-woven fibrous material having the characteristics of high wet-strength and low fluid absorbency. It may be more specifically constructed of cellulosic material or other material having the common descriptive qualities of paper, or other materials of synthetic fibers. For added strength, this non-woven material may be reinforced with a network of threads of nylon or other strong material. A drape material currently available from the Kimberly-Clark Company under the trademark "Kaycel" is very suitable. A lamination combining the reinforcement layer 44 and liquid-impermeable layer 46 is available as an adhesive-backed sheet material sold under the trademark "Dri-Site". An inner reinforcing layer 48 (see FIG. 16) is preferred, and may be constructed of the "Kaycel" material aforementioned. A limb-covering sock may be made of a liquid-resistant material available from the DuPont Company under the trademark "Tyvek".

One of the main objects of the present invention is to provide a compact, surgical drape which minimizes contamination in applying the drape. To achieve this objective, the covering 38 is collapsed to the surface of sheet 34 so as to sequentially expose longitudinal portions which are of greater diameter as the limb is advanced through the fenestration 36. Two different suggested forms of collapsing covering 38 are shown in FIGS. 4 and 4A. The covering 38 is illustrated in FIG. 4 and includes a plurality of longitudinal sections 50 of increasing diameter, which is a natural function of the generally conical shaped covering 38. By telescopically collapsing the segments 50, one inside the other, the telescopic sections 50 are exposed as a limb is moved through fenestration 36. The sequence of unravelling or progressive exposure of such portions of increasing diameter are specifically shown in FIGS. 21 and 22. A limb, in this case an arm 52, is initially inserted and comes in contact with the end 42 at the smallest diameter section of covering 38. As the limb continues to move through, the larger portions are exposed to the limb. By providing such a sequential exposure of increasing diameter sections, the interior of covering 38 only comes in contact with that portion of the limb to which it is adjacent. This reduces the possibility of contaminating the specific area of the surgery on the limb by unprepared or unsterile portions of the limb coming in contact with the total interior of the covering 38.

By sequentially exposing portions of increasing diameter, a contoured (yet loosely fitting) covering is provided for varying lengths and widths of limbs. Thus, for shorter (which are generally smaller diameter) limbs, the smaller diameter portions only are dispensed, and they contour to — but do not snugly engage — the limbs, leaving the larger diameter portions collapsed. This differs from the prior art which either provides a tight fitting stockinette or a totally baggy enclosure for limbs. By providing a contoured, yet not snug-fitting, covering, access to the site of surgery on the limb may be accurately and completely isolated from the remainder of the limb and the contamination of the total interior covering 38 is reduced to a minimum.

A second method of collapsing the covering 38 is shown in FIG. 4A to have a generally accordian-shape fold. In this type of fold, the portions of increasing diameter 52 lie one on top of the other in planes parallel to the plane of sheet 34. Similar to the fold of FIG. 4, portions 52 of increased diameter are sequentially exposed as the limb is advanced through fenestration 36.

Figure 7:
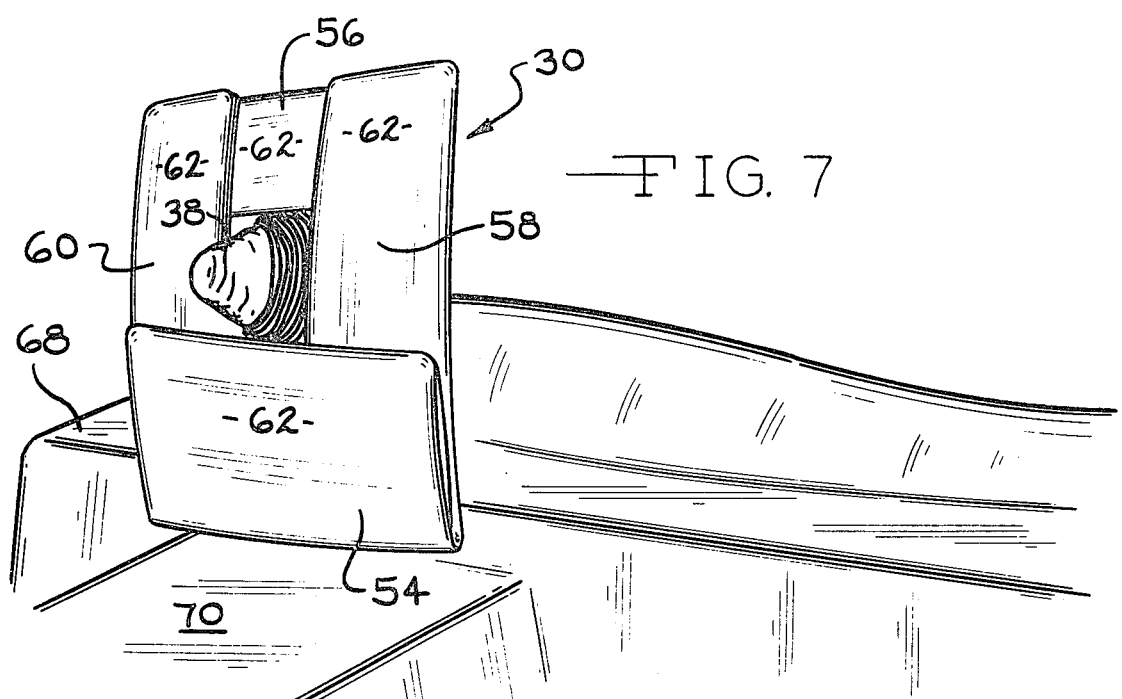

FIGS. 5 and 7 illustrate the drape 30 of FIG. 1 folded and collapsed in its packaged condition. Covering 38 is collapsed using the telescopic form of FIG. 4 and the sheet 34 is folded so as to provide four folded stacks completely surrounding the collapsed covering 38. The four folded stacks are overlapping so as to have a topmost stack 54, a bottom stack 56 and two intermediate folded stacks 58, 60. Sheet 34, having a patient side 62 and an external side 64, is folded so as to have none of the external sides 64 exposed in the folded position. This keeps the external side, which is sterile, free of contamination in the packaged condition and reduces the contamination probability from the process of applying the drape to the surgical patient.

Figure 8:
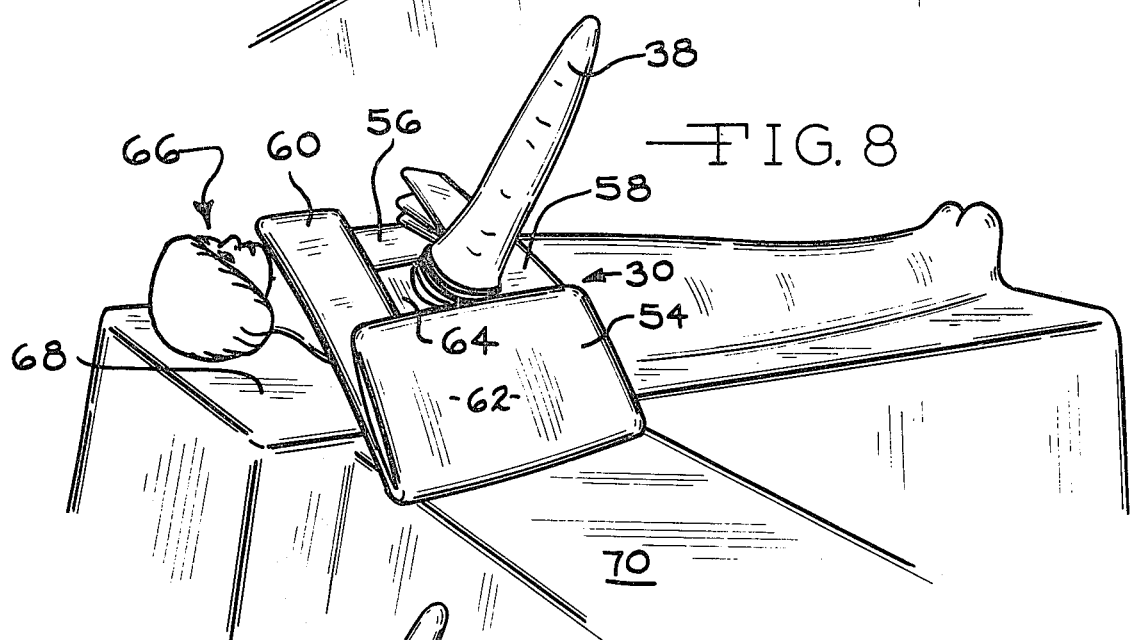

The process for applying the surgical drape 30 of FIGS. 1 and 5 to an upper extremity is illustrated in FIGS. 7-15. The surgical patient 66 is positioned on a surgical table 68 having an auxiliary table or surface 70 upon which the limb will rest during surgery. The drape 30 is unpackaged and handled by the doctor or nurse by the surface 62 which will be right next to the patient during the operation. The patient's arm is directed through fenestration 36 so that portions of covering 38 of increasing diameter are sequentially exposed to the limb as shown in FIG. 7. Once the limb is completely extended into covering 38 as shown in FIG. 8, the four folded stacks of the drape lie upon the patient. As illustrated in FIG. 8, the unexposed portions of sleeve 38 lie collapsed upon the sheet 34. It should be noted that the collapsible sleeve 38 shown in FIGS. 7-15 is the accordian-like fold of FIG. 4A, though the telescopic fold of FIG. 4 may be used.

Figure 9:
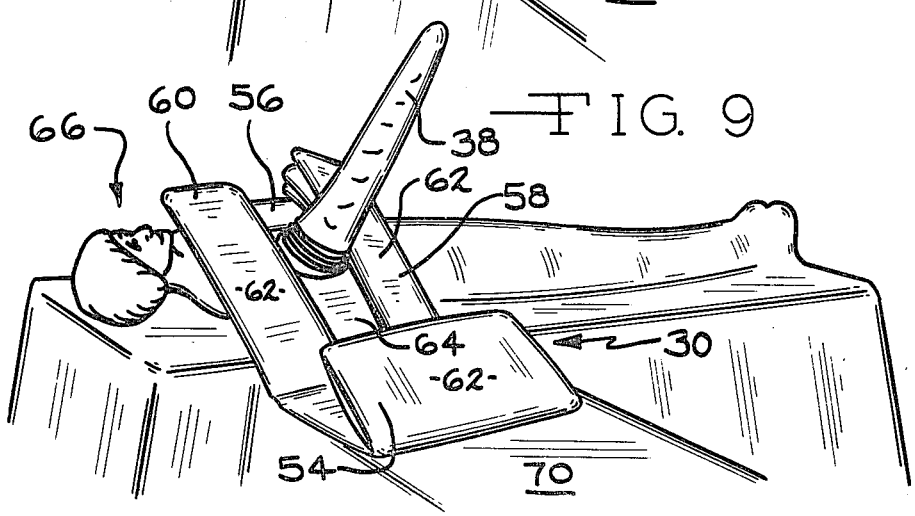
Figure 10:
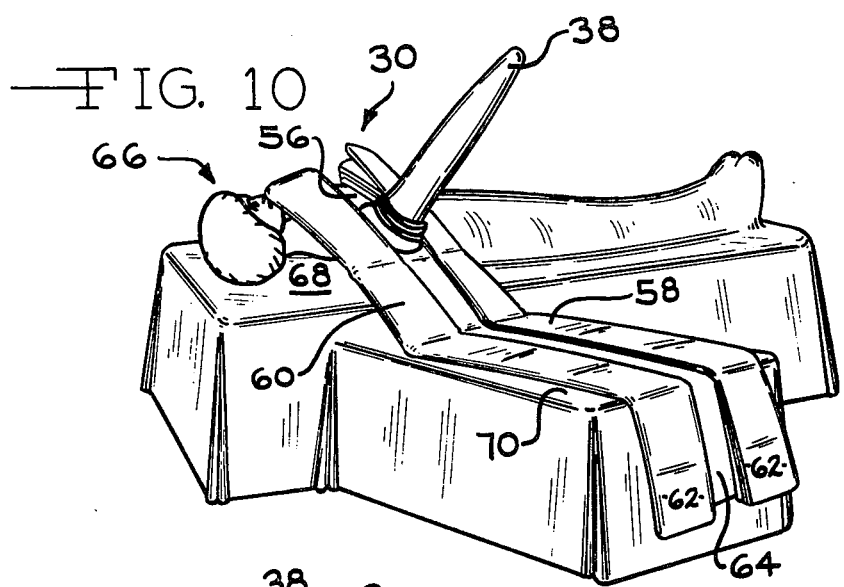
Figure 11:
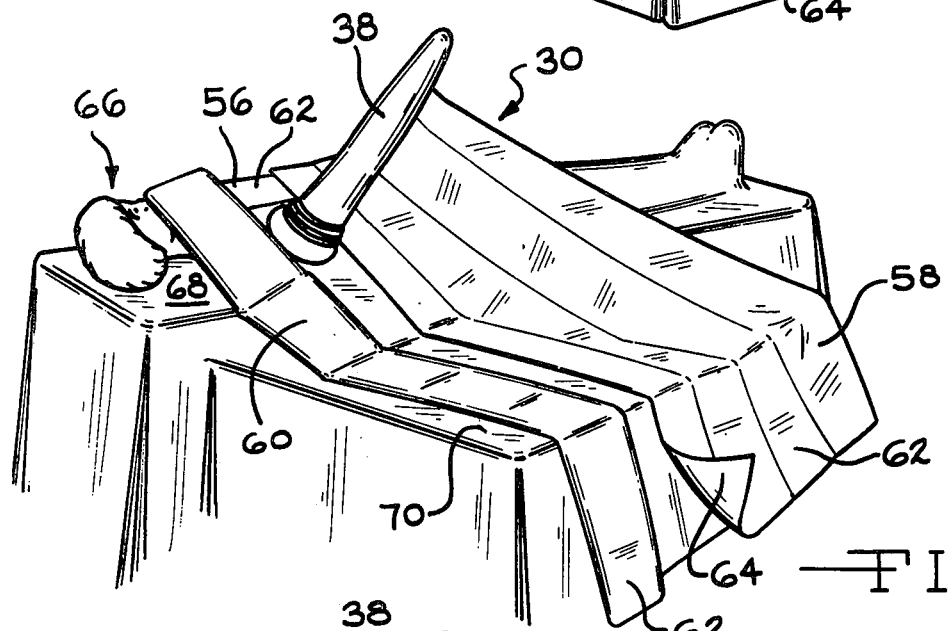

Once the limb is completely inserted in the sleeve 38 (FIG. 8), the topmost stack 54 is unfolded away from the body along platform or table 70 (FIG. 9). It should be noted that the first unfolded section is the section upon which the limb will rest during surgery. By unfolding stack 54 as illustrated in FIGS. 8 and 9 to the final position as shown in FIG. 10, the first external or sterile portion 64 of sheet 34 is exposed. After stack 54 has been totally unfolded, stack 58 (which is folded at 90° relative to the original stack 54) is unfolded along the length of patient 66. As illustrated in FIG. 11, stack 58 is unfolded up to its last fold with the patient surface 62 only exposed and the last unfold reveals sterile surface 64. By reducing the amount of time that the sterile surface 64 is exposed and/or handled during the unfolding operation of the four stacks, the probability of contamination of sterile surface 64 is greatly reduced.

Figure 12:
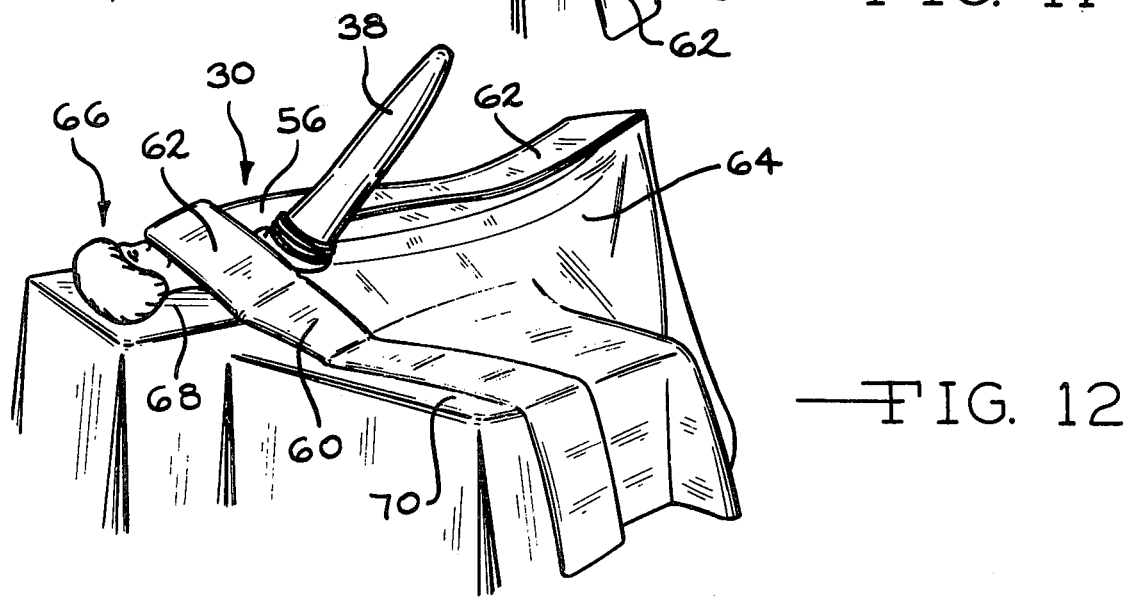

The next stack to be unfolded is the other intermediate stack 60 which is opposite the originally unfolded stack 58 and is folded 90° relative to the original stack 54. This stack is also unfolded along the length of the patient, though not covering the head of the patient, as illustrated in FIGS. 12 and 13. The final stack to be unfolded is the bottom stack 56 which is opposite the original stack 54. This stack is unfolded as illustrated in FIGS. 14 and 15 so as to completely cover the patient and isolate the patient from the surgical team. The patient as illustrated in FIG. 15 is now ready for surgery. An opening (not shown) is then cut in covering 38 to expose the area of surgery. By completely covering the patient and isolating the limb upon which the surgery is to be performed, the area of surgery is totally isolated from the patient in the covering 38 and the patient is totally isolated from the surgical team.

The surgical drape 32 for lower extremities or limbs is shown being applied to the patient in FIGS. 16-20. The folded drape 32 is placed over a leg or limb 72, as shown in FIG. 16, which is then advanced through fenestration 36 so as to sequentially expose portions of covering 38. As noted in FIG. 17, the covering 38 may be flexible enough so as to contour to the foot portion at an angle relative to the longitudinal axis of covering 38. Once the limb 72 is completely encased in covering 38, the four folded stacks of drape 32 are unfolded. The folded stacks are overlapping so as to have two topmost stacks 74 and 76 opposite each other and two bottom stacks 78 and 80 opposite each other and at 90° relative to the topmost stacks 74 and 76. As with the folded drape 30, the drape 32 in the folded position has substantially none of the sterile area 64 exposed.

Figure 18:
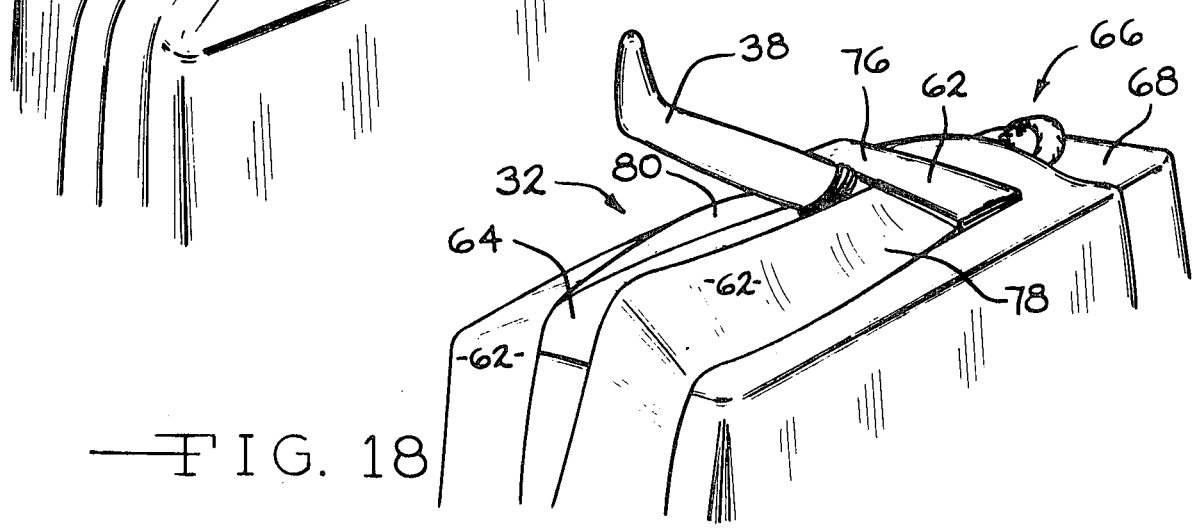

Once the drape 32 is in place, the folded stack 74 is unfolded along the length of the body so as to expose portions 64 and define the area upon which the covered limb will rest during surgery. This is similar to the fold or drape 30 wherein the first unfolded stack is that which will support the limb during surgery. Once stack 74 is unfolded as shown in FIG. 18, the other topmost stack 76 is unfolded along the length of the body leaving a single unfolded flat section as shown in FIG. 19. Next, stack 78 is unfolded across the body and finally stack 80 is also unfolded across the body. If desired, the single unfolded flap of stack 76 may be attached or secured to supports or standards 82. The patient is now ready for surgery with the patient being totally isolated from the surgical team and the limb upon which the surgery is to be performed is isolated from the patient. An opening (not shown) is then cut in covering 38 to provide access to the surgical site.

To completely isolate the patient from the surgical site, a single strap or a plurality of straps 84 may be provided (FIG. 23) which encompass the covering 38 to divide the covering so as to isolate the area of surgery from the fenestration 36. Such straps also serve to preclude slipping of the limb covering around the limb, so that the surgical opening in the covering remains in register with the surgical site on the limb. These straps may be made or have surfaces of Velcro to provide a high degree of adjustability for different diameter limbs.

A modification of covering 38 as shown in FIG. 24 includes a section 86 which is enlarged relative to the covering 38 and is secured between the base of covering 38 and the sheet 34. The enlarged section 86 accommodates medical equipment attached to the limb upon which surgery is to be performed, for example, the pressurized tourniquet 88 illustrated in FIG. 24. Though illustrating a specific piece of equipment, it is obvious that other pieces of equipment or monitoring devices may be attached and accommodated in section 86.

From the above procedures, it is obvious that the present invention provides a disposable surgical drape for orthopedic or other operative procedures for the upper and/or lower extremities. The drape is packaged in a compact, collapsed and folded manner which allows the doctor and nurses applying the drape to grasp the surface of the drape which will contact the patient and avoid touching the surface which will become exposed to the surgical team, at the same time sliding the covering onto the limb and unfolding the drape to cover the entire patient. This eliminates the likelihood that the contaminated portion, which has come in direct contact with the unprepared and sterile portion of the patient or equipment, would be handled or touched by the doctor or nurse. The entire draping procedure is executed in a single phase in a fashion which is allowed by the unitary construction of the limb covering and the sheet, thereby eliminating time-consuming step-by-step methods, reducing the risk of prolonged anesthesia and the possibility of infecting the patient.

From the preceding description of the preferred embodiments, it is evident that the objects of the invention are obtained. Although the invention has been described and illustrated in detail, it is to be clearly understood that the same is by way of illustration and example only and is not to be taken by way of limitation. The essence of the invention is the provision of an integral draping system for limbs upon which surgery is to be performed, which isolates the limbs and is applied in such a way as to reduce the probability of contamination. The spirit and scope of this invention are limited only by the terms of the appended claims.

What is claimed:

1. A surgical drape for covering a surgery patient and isolating an extremity upon which surgery is to be performed, said drape comprising:

a generally rectangular sheet having a patient surface and an exterior surface;

a fenestration in said sheet for receiving said extremity and isolating said extremity relative to the rest of the patient's body;

an elongate limb covering mounted at its base to said sheet and over said fenestration for receiving said extremity;

said sheet being foldable about said covering so that substantially no exterior surface of said sheet is exposed; and said covering is somewhat conical and collapsible so as to sequentially expose longitudinal portions of greater diameter as said extremity is advanced through said fenestration.

2. The surgical drape of claim 1 wherein said covering is collapsed telescopically so that said sequential longitudinal portions are one inside the other.

3. The surgical drape of claim 1 wherein said covering is collapsed accordion-like with said sequential longitudinal portions disposed one on top of the other.

4. The surgical drape of claim 1 wherein said base of said covering is mounted to said patient side of said sheet and includes a piece of material mounted to said patient side of said sheet contiguous to said fenestration and covering said base mounting for reinforcing said fenestration and base mounting.

5. The surgical drape of claim 4 wherein said sheet is constructed of non-woven, disposable material.

6. The surgical drape of claim 5 including a piece of liquid-impermeable material mounted to said exterior side of said sheet contiguous to said fenestration.

7. The surgical drape of claim 1 wherein said sheet is folded so that said covering is surrounded by four folded stacks of said sheet.

8. The surgical drape of claim 7 wherein said foldable stacks are overlapping so that the topmost stack unfolds away from said patient, the bottom stack, which is opposite said topmost stack, unfolds across said patient, and two intermediate stacks, which are opposite each other and folded at right angles to the topmost and bottom stacks, unfold along the length of said patient.

9. The surgical drape of claim 8 wherein the first unfolded stack provides the surface upon which said extremity will rest during surgery.

10. The surgical drape of claim 1 wherein said sheet folds to surround said covering with four folded stacks of said sheet.

11. The surgical drape of claim 10 wherein said foldable stacks are overlapping so that the topmost stack unfolds away from said patient, the bottom stack, which is opposite said topmost stack, unfolds across said patient, and two intermediate stacks, which are opposite each other and folded at right angles to the topmost and bottom stacks, unfold along the length of said patient.

12. The surgical drape of claim 11 including at least one strap which encompasses said covering for dividing said covering to isolate the area of surgery from said fenestration.

13. The surgical drape of claim 7 wherein said foldable stacks are overlapping so that two of said folded stacks, which are opposite each other, are topmost and unfold along the length of said patient and the other two stacks, which are opposite each other, and at right angles to the topmost stacks, unfold away from said patient at right angles to said length.

14. The surgical drape of claim 10 wherein said foldable stacks are overlapping so that two of said folded stacks, which are opposite each other, are topmost and unfold along the length of said patient and the other two stacks, which are opposite each other, and at right angles to the topmost stacks, unfold away from said patient at right angles to said length.

15. The surgical drape of claim 14 including at least one strap which encompasses said covering for dividing said covering to isolate the area of surgery from said fenestration.

16. The surgical drape of claim 1 including at least one strap which encompasses said covering for dividing said covering to isolate the area of surgery from said fenestration.

17. The surgical drape of claim 11 wherein said sheet is of sufficient length and width to completely cover said patient and to isolate the patient from the surgical team and the area of surgery.

18. The surgical drape of claim 17 wherein said covering includes an enlarged section between said base and said sheet to accommodate a tourniquet.

19. The surgical drape of claim 14 wherein said sheet is of sufficient length and width to completely cover said patient and to isolate the patient from the surgical team and the area of surgery.

20. The surgical drape of claim 19 wherein said covering includes an enlarged section between said base and said sheet to accommodate a tourniquet.

21. The surgical drape of claim 1 wherein said covering includes an enlarged section between said base and said sheet to accommodate a tourniquet.

* * * * *